US010555760B2

(12) United States Patent
Buttermann

(10) Patent No.: US 10,555,760 B2
(45) Date of Patent: Feb. 11, 2020

(54) BONE ATTACHMENT ASSEMBLY

(71) Applicant: GLOBUS MEDICAL, INC., Audubon, PA (US)

(72) Inventor: Glenn R. Buttermann, Mahtomedi, MN (US)

(73) Assignee: Globus Medical, Inc., Audubon, PA (US)

(*) Notice: Subject to any disclaimer, the term of this patent is extended or adjusted under 35 U.S.C. 154(b) by 43 days.

(21) Appl. No.: 15/526,582

(22) PCT Filed: Nov. 12, 2015

(86) PCT No.: PCT/US2015/060445
§ 371 (c)(1),
(2) Date: May 12, 2017

(87) PCT Pub. No.: WO2016/077621
PCT Pub. Date: May 19, 2016

(65) Prior Publication Data
US 2018/0289397 A1      Oct. 11, 2018

Related U.S. Application Data

(60) Provisional application No. 62/079,355, filed on Nov. 13, 2014.

(51) Int. Cl.
*A61B 17/70* (2006.01)
*A61B 17/88* (2006.01)
(Continued)

(52) U.S. Cl.
CPC ...... *A61B 17/7032* (2013.01); *A61B 17/7002* (2013.01); *A61B 17/7037* (2013.01);
(Continued)

(58) Field of Classification Search
CPC ............ A61B 17/7032; A61B 17/7002; A61B 17/7037; A61B 17/7038; A61B 17/7034;
(Continued)

(56) References Cited

U.S. PATENT DOCUMENTS 5,346,493 A    9/1994  Stahurski et al.
7,678,137 B2   3/2010  Butler et al.
(Continued)

FOREIGN PATENT DOCUMENTS

WO    2013126744 A2    8/2013
WO    2014164490 A1    10/2014

OTHER PUBLICATIONS

International Search Report and Written Opinion of the International Searching Authority in corresponding International Application No. PCT/US2015/060445 dated Feb. 23, 2016, 10 pages.
(Continued)

*Primary Examiner* — Pedro Philogene
*Assistant Examiner* — David C Comstock

(57) ABSTRACT

A bone attachment assembly may include an attachment head, a set screw configured to attach to the attachment head, and a rod surface with a first raised portion and a second raised portion that define a lowered portion positioned between the first raised portion and the second raised portion. The first raised portion, the second raised portion, and the set screw may be configured to directly contact a rod in order to retain the rod within the attachment head.

14 Claims, 15 Drawing Sheets

(51) Int. Cl.
*A61B 90/00* (2016.01)
*A61B 17/56* (2006.01)

(52) U.S. Cl.
CPC ...... *A61B 17/7038* (2013.01); *A61B 17/7047* (2013.01); *A61B 17/7034* (2013.01); *A61B 2017/564* (2013.01); *A61B 2090/037* (2016.02)

(58) Field of Classification Search
CPC .......... A61B 17/7047; A61B 2090/037; A61B 2017/564
USPC ........ 606/264, 265, 267, 270, 272, 308, 320
See application file for complete search history.

(56) References Cited

U.S. PATENT DOCUMENTS

| | | | |
|---|---|---|---|
| 8,097,025 B2 | 1/2012 | Hawkes et al. | |
| 8,221,472 B2 | 7/2012 | Peterson et al. | |
| 8,388,659 B1* | 3/2013 | Lab | A61B 17/7037 606/265 |
| 8,852,239 B2 | 10/2014 | Jackson et al. | |
| 2008/0177260 A1 | 7/2008 | McKinley et al. | |
| 2010/0094343 A1* | 4/2010 | Pham | A61B 17/7038 606/246 |
| 2010/0298891 A1 | 11/2010 | Jackson | |
| 2011/0257690 A1* | 10/2011 | Rezach | A61B 17/7037 606/302 |
| 2013/0184770 A1 | 7/2013 | Buttermann | |

OTHER PUBLICATIONS

International Preliminary Report on Patentability and Transmittal received in corresponding International Application No. PCT/US2015/060445 dated May 26, 2017, 8 pages.

* cited by examiner

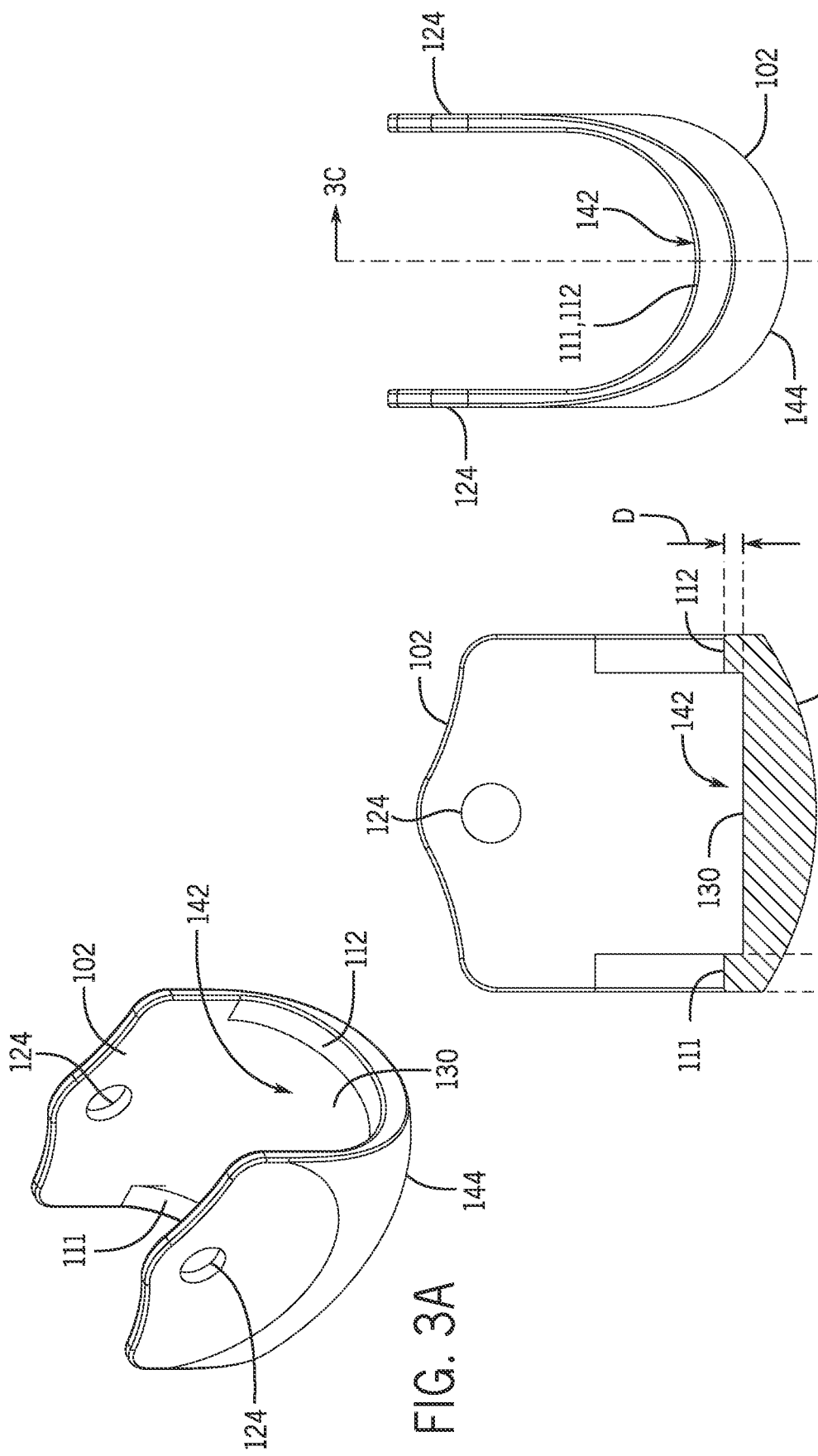

BONE ATTACHMENT ASSEMBLY

CROSS-REFERENCE TO RELATED PATENT APPLICATIONS

The present application is a U.S. National Stage of International Application No. PCT/US2015/060445 filed on Nov. 12, 2015, which claims the benefit of U.S. Provisional Patent Application No. 62/079,355 filed on Nov. 13, 2014, the entire disclosures of all of which are incorporated herein by reference.

FIELD

This disclosure relates generally to bone attachment assemblies and methods of assembling a bone attachment assembly.

BACKGROUND

During spinal fusion surgery, bone attachment assemblies can be attached to bones. For example, bone screws, such as vertebral screws, may be fixed to adjacent vertebrae. Hooks or clamps may also be fixed to vertebra or ribs. The bone attachment assemblies that include bone screws, hooks, and/or clamps, may be interconnected to each other by a rod that attaches with multiple bone screws, hooks, and/or clamps in order to stabilize the spine during the healing process. The rods interconnecting the bone attachment assemblies may span one or more vertebral levels (e.g., one to three vertebral levels for a spinal fusion of a degenerative condition, eight to twelve vertebral levels for scoliosis, etc.).

In order to attach with a rod or connector, the bone attachment assemblies may include an attachment head with a slot that is intended to receive the rod. The rod may be at least partially secured within the slot by a cap or set screw.

Bone screws may be classified as monoaxial, polyaxial, or uniplanar based on their adjustability. Monoaxial bone attachment assemblies, such as monoaxial bone screws, are the most simplistic and are not particularly versatile in connection with accommodating screw placement and alignment. The attachment head of a monoaxial bone screw may allow the rod to be adjusted in only one direction, perpendicular to the longitudinal axis of the screw. When the rod is secured in the slot of the monoaxial bone screw, the longitudinal axis of the rod is substantially perpendicular (i.e., at approximately a 90° angle to) to the longitudinal axis of the monoaxial bone screw.

Polyaxial bone attachment assemblies, such as polyaxial screws, are commonly used to overcome the variations in screw placement and alignment. The relationship between the screw axis and the rod axis in a polyaxial screw may be adjustable but may still be locked in place (e.g., the attachment head of a polyaxial screw (and thus the rod) may be configured to swivel approximately 20° off the screw axis when unlocked). This adjustability may allow rods to be connected to multiple screws that may be placed medial or lateral to one another and may permit lordotic and kyphotic spinal alignments. Conventional polyaxial screws are typically larger and bulkier than monoaxial screws due to, for example, the structures that allow the attachment head of the polyaxial screw to swivel.

Uniplanar bone attachment assemblies, such as uniplanar screws, may have attachment heads that allow the rod be adjusted or moved within one plane relative to the screw axis. Typically, uniplanar screws do not allow the rod to be adjusted to medial or lateral rod positions (unlike polyaxial screws). Uniplanar screws are more commonly used in scoliosis surgery where there may be a degree of cranial or caudal angulation (such as the sagittal plane of the spine), but where there is little medial lateral screw placement deviation and the surgeon additionally needs rigid control of the screw to manipulate it in the coronal and axial plane of the spine. Similar to polyaxial screws, uniplanar screws generally are large and bulky due to the configuration of their single plane swivel mechanism.

The connecting rods that can attach with and connect to multiple bone attachment assemblies, such as bone screws, experience significant loads from the secured bone attachment assemblies attached to the patient for correction. Such loads may cause the connecting rods to slip within the bone attachment assemblies.

Monoaxial bone screws, which are designed to receive and secure a connecting rod at a fixed angle (such as 90 degrees) with respect to the screw shaft, may include a recess formed in the attachment head of the monoaxial bone screw to permit increased loads to be applied to a connecting rods disposed therein. However the rigid structure of such monoaxial bone screws disadvantageously constrains the mobility of a connecting rod held therein, such that movement of the rod away from the fixed angle eliminates contact points between the monoaxial bone screw and the connecting rod, thereby increasing the risk of rod slippage.

SUMMARY

A bone attachment assembly may include an attachment head, a set screw configured to attach to the attachment head, and a rod surface with a first raised portion and a second raised portion that define a lowered portion positioned between the first raised portion and the second raised portion. The first raised portion, the second raised portion, and the set screw may be configured to directly contact a rod in order to retain the rod within the attachment head.

A method of assembling a bone attachment assembly may include positioning a rod within an attachment head such that the rod directly contacts a first raised portion and a second raised portion of the rod surface, attaching a set screw to the attachment head, and advancing the set screw along the attachment head toward the rod such that the set screw directly contacts and applies a point load to the rod. The first raised portion and the second raised portion define a lowered portion positioned between the first raised portion and the second raised portion, the first raised portion, the second raised portion, and the set screw retain the rod within the attachment head.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

Features, aspects, and advantages of the present invention will become apparent from the following description and the accompanying exemplary embodiments shown in the drawings, which are briefly described below.

FIG. 3A is a perspective view of a rod carrier that can be disposed in the bone attachment assembly of FIG. 1A.

FIG. 3B is an end view of the rod carrier of FIG. 3A.

FIG. 3C is a cross-sectional view of FIG. 3B along line 3C-3C.

DETAILED DESCRIPTION

Following below are more detailed descriptions of various concepts related to, and embodiments of, inventive apparatuses and methods for a bone attachment assembly. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Referring generally to the figures, disclosed herein is a bone attachment assembly and a method of assembly a bone attachment assembly, as shown according to exemplary embodiments, which may be used to align a spine of a patient. According to one embodiment, the bone attachment assembly may be a uniplanar bone attachment assembly, such as a side-loading or top-loading low-profile, uniplanar bone attachment assembly. According to another embodiment, the bone attachment assembly may be a polyaxial bone attachment assembly. The bone attachment assembly may be a bone screw assembly, a bone hook assembly, a bone clamp assembly, or any combination thereof.

According to one embodiment and as described further herein, the bone attachment assembly may be configured to secure a connecting rod within an attachment head of the bone attachment assembly. In order to more securely retain with the rod, a rod carrier that is movable within the attachment head and a set screw attachable to the attachment head may be specifically shaped in order to provide a three-point attachment with the rod. More specifically, the rod carrier may include two raised portions and the set screw may include a pointed tip to directly contact and securely retain the rod within the attachment head.

Bone Attachment Assembly

Figure 1A:
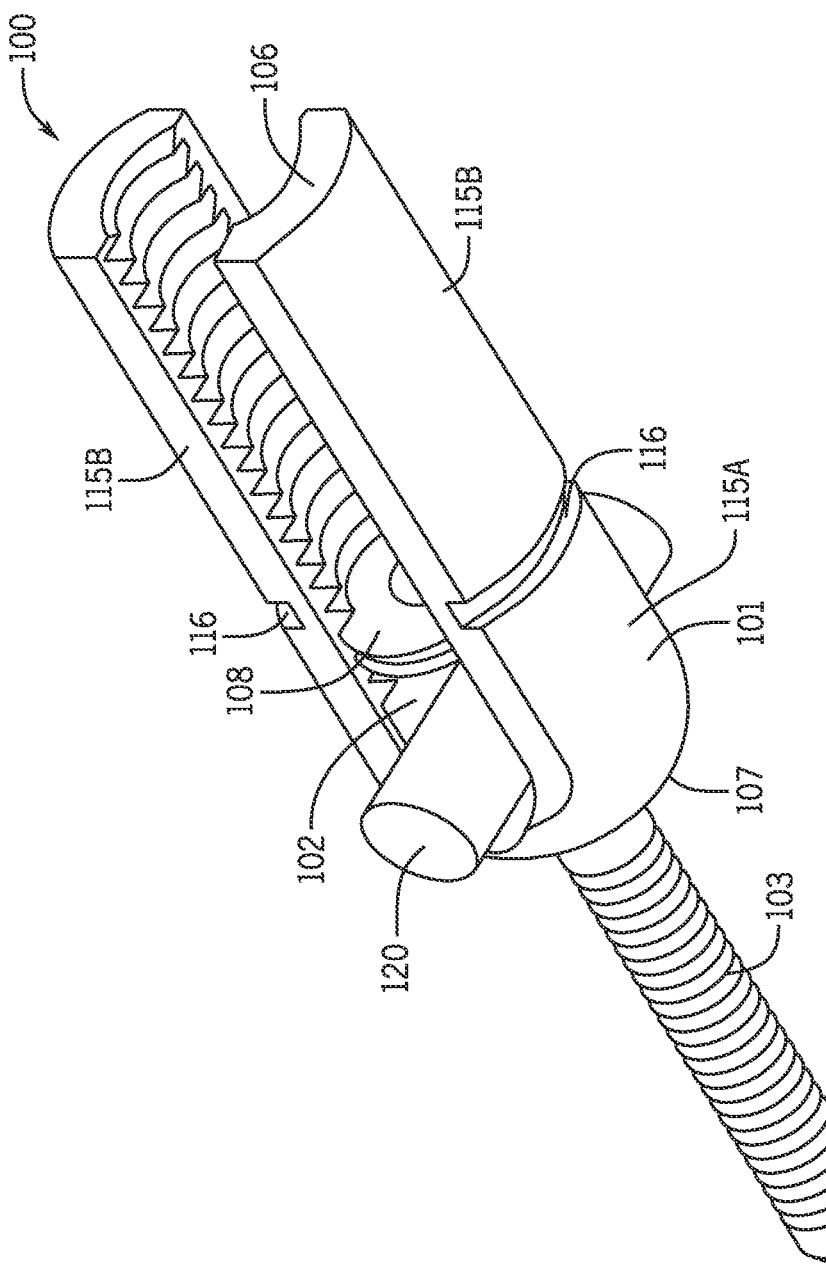
FIG. 1A is a perspective view of a bone attachment assembly according to one embodiment of the present invention.
Figure 1B:
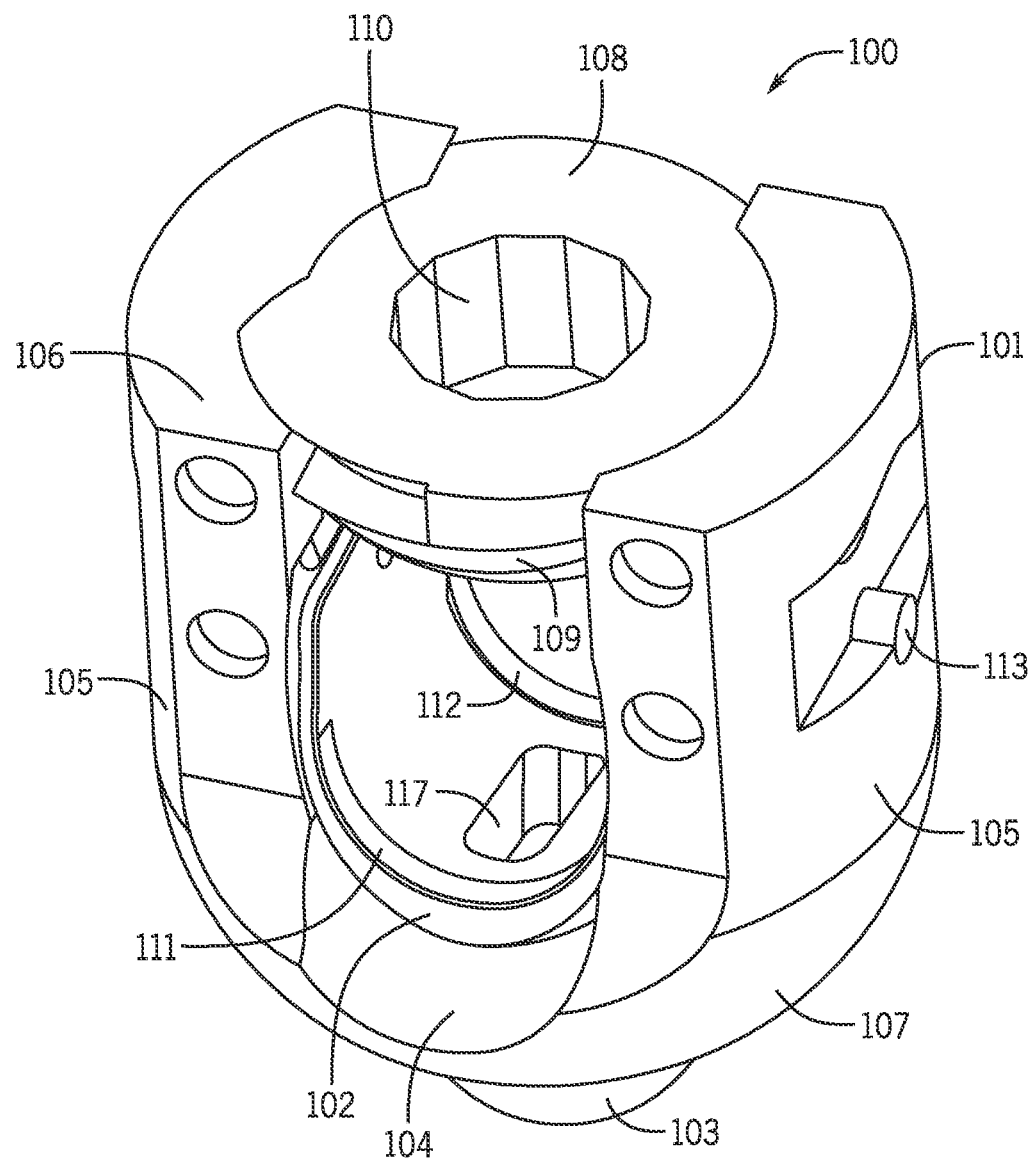
FIG. 1B is a perspective, partial view of the bone attachment assembly of FIG. 1A without the connecting rod.
Figure 1C:
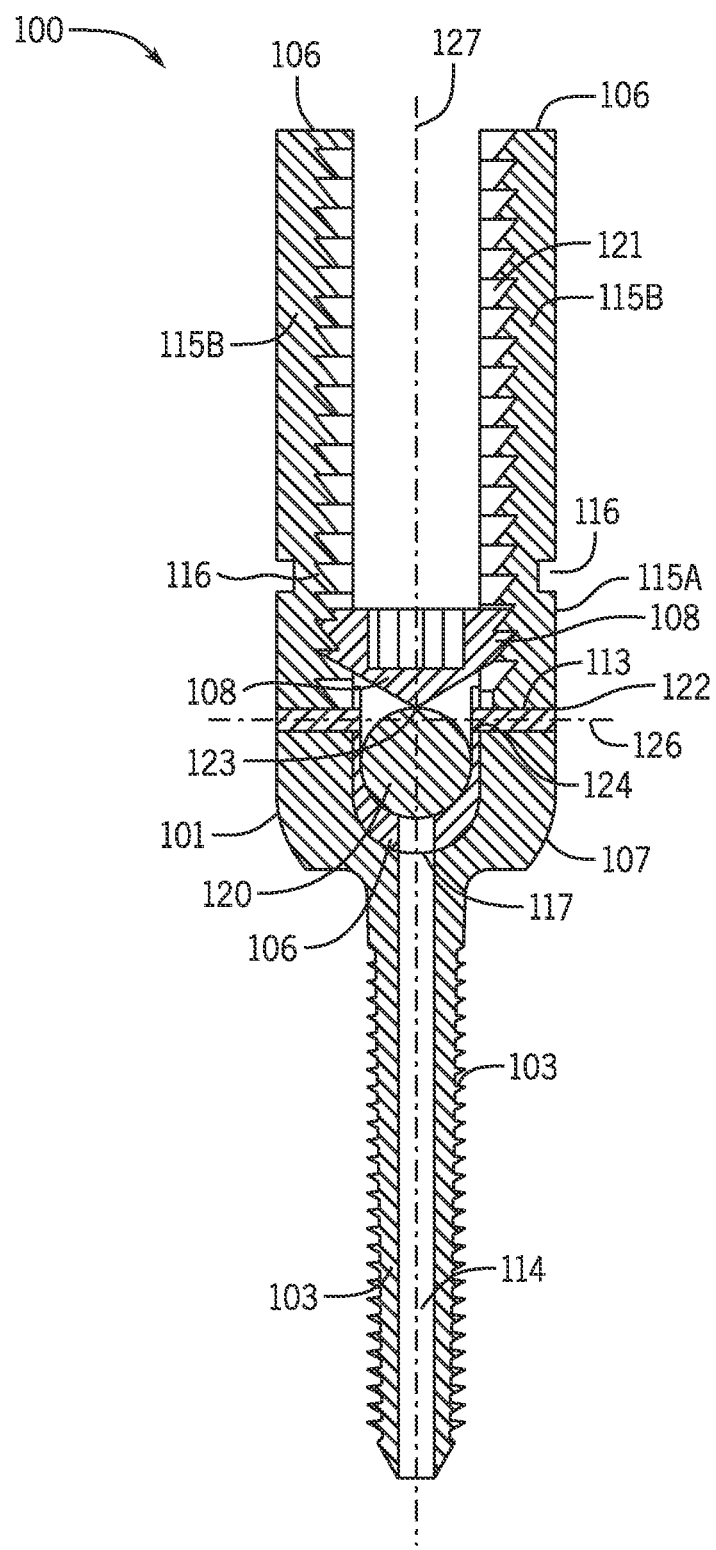
FIG. 1C is a cross-sectional view of the bone attachment assembly of FIG. 1A.
Figure 9:
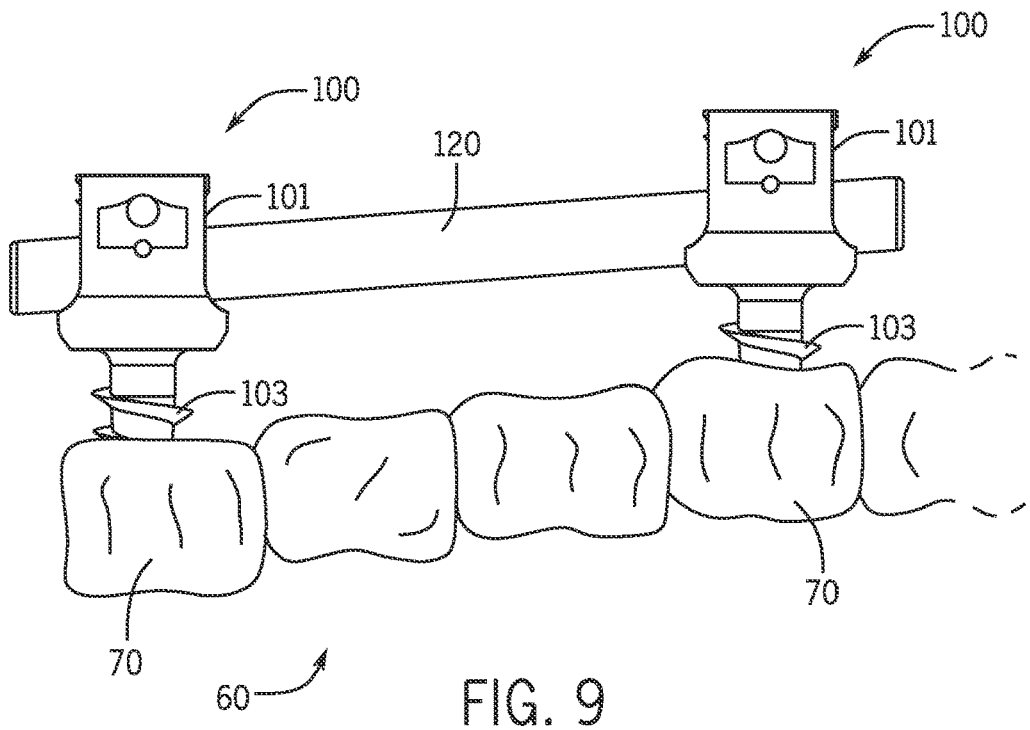
FIG. 9 is a schematic representation of bone attachment assemblies attached to bone according to one embodiment.
Figure 12:
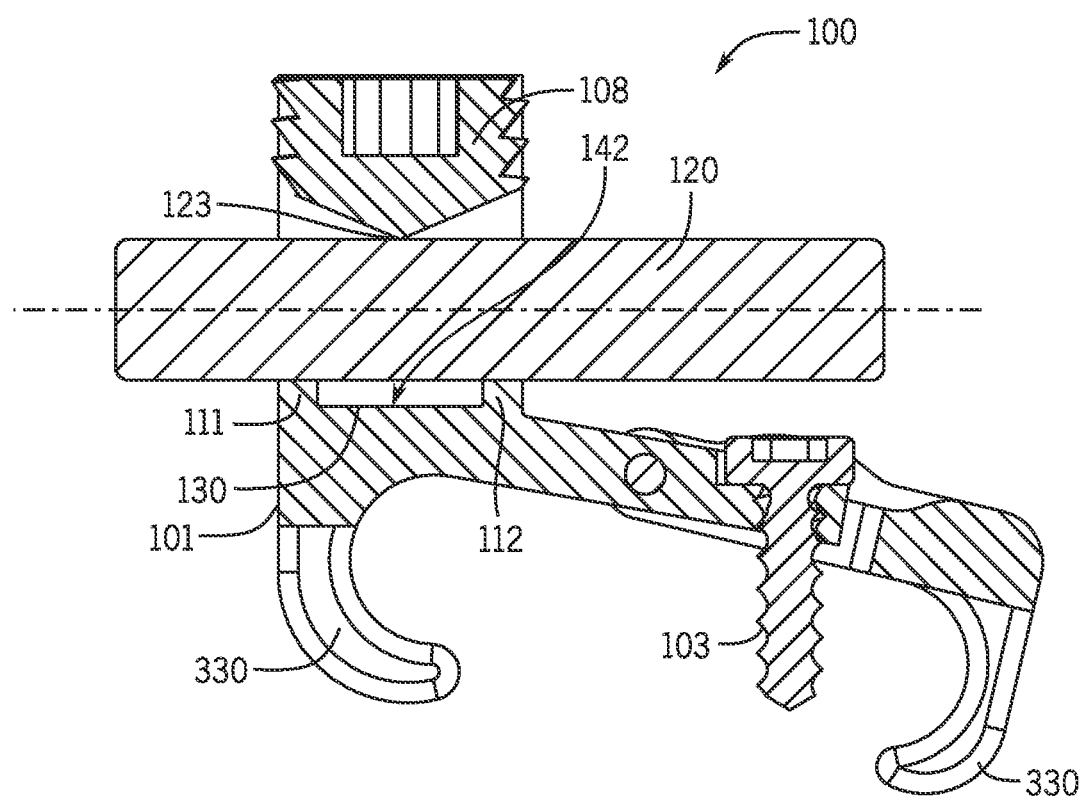
FIG. 12 is a cross-sectional view of a bone attachment assembly according to yet another embodiment.

FIGS. 1A-1C illustrate one embodiment of a bone attachment assembly 100. As described further herein, the bone attachment assembly 100 may include a screw head or attachment head 101 that can hold a connecting rod 120 to attach the connecting rod 120 to bone 70 via a threaded screw shaft 103 that can be screwed into bone 70, as shown in FIG. 9 or via hooks or clamps 330 (and optionally a threaded screw shaft 103), as shown in FIG. 12, that can attach around a portion of the bone 70.

Connecting Rod

As shown in FIG. 1A, the connecting rod 120 may be positioned within or extend through and be secured within or retained by the attachment head 101 of the bone attachment assembly 100. According to one embodiment, the bone attachment assembly 100 may include the connecting rod 120.

The connecting rod 120 may be formed of any conventional materials and in accordance with conventional constructions of connecting rods know to a person skilled in the art. Other or new connecting rod materials or constructions could also be used with the bone attachment assembly 100.

Figure 4A:
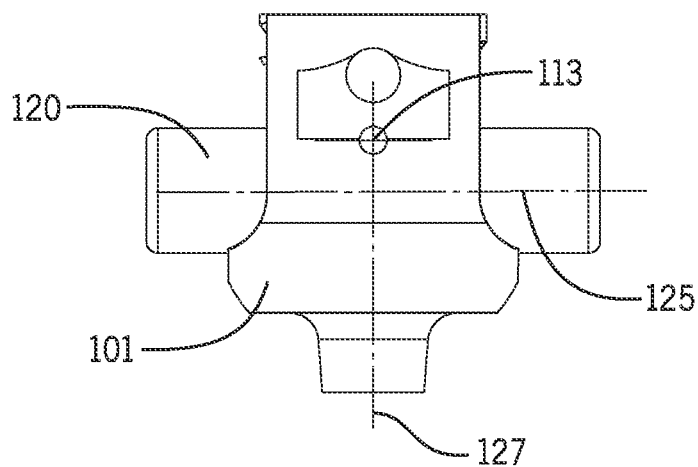
FIG. 4A is a side view of the bone attachment assembly of FIG. 1B with a rod in a first position.
Figure 5A:
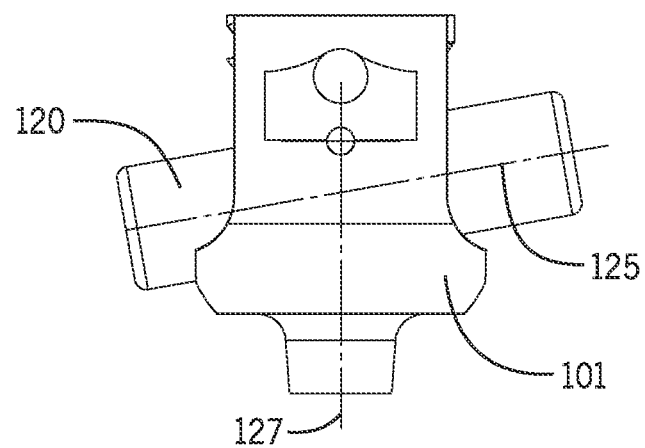
FIG. 5A is a side view of the bone attachment assembly of FIG. 1B with a rod in a second position.

As described further herein, the rod 120 may be positioned within and through a channel 104 of the attachment head 101 and may be secured between a rod surface 142 and a set screw 108 such that the rod 120 directly contacts the first raised portion 111, the second raised portion 112, and the set screw 108. As shown in FIG. 4A, the rod 120 may be positioned within the attachment head 101 such that the longitudinal rod axis 125 of the rod 120 is substantially perpendicular to the longitudinal screw axis 127 of the threaded screw shaft 103. However, due to a rod carrier 102, the position of the rod 120 may be adjusted such that the longitudinal rod axis 125 of the rod 120 is not substantially perpendicular to the longitudinal screw axis 127 of the threaded screw shaft 103, as shown in FIG. 5A.

As shown in FIG. 9, the rod 120 may also extend through and be secured within at least one other attachment head of at least one other bone attachment assembly 100, thereby connecting one or more bone attachment assemblies together along a length of the spine 60. The bone attachment assemblies 100 can each be screwed and secured into the bone 70.

Threaded Screw Shaft

The threaded screw shaft 103 may be configured to be screwed or inserted into the bone upon rotatably advancing the screw shaft 103 in order to fix the bone attachment assembly 100 to the bone. Accordingly, the threaded screw shaft 103 may include a pointed tip in order to guide the screw shaft 103 into and through the bone. The threaded screw shaft 103 may extend along a longitudinal screw axis 127 of the bone attachment assembly 100, as shown in FIG. 1C.

According to one embodiment as shown in FIG. 1C, the screw shaft 103 may be cannulated and thus may include a cannula conduit 114 that extends along the longitudinal axis of the screw shaft 103. However, according to an alternative embodiment as shown in FIG. 6C, the screw shaft may not be cannulated and instead may be substantially solid.

Attachment Head

The attachment head 101 may be used to retain and partially enclose the rod 120. Accordingly, the attachment head 101 may include a plurality of sidewalls 105 forming a channel 104 for the rod 120 to extend through. The channel 104 may extend through the attachment head 101 from a first side of the attachment head 101 to a second side of the attachment head 101. The channel 104 may descend from a top region 106 of the attachment head 101 to a base region 107 of the attachment head 101 along the longitudinal screw axis 127.

Figure 2:
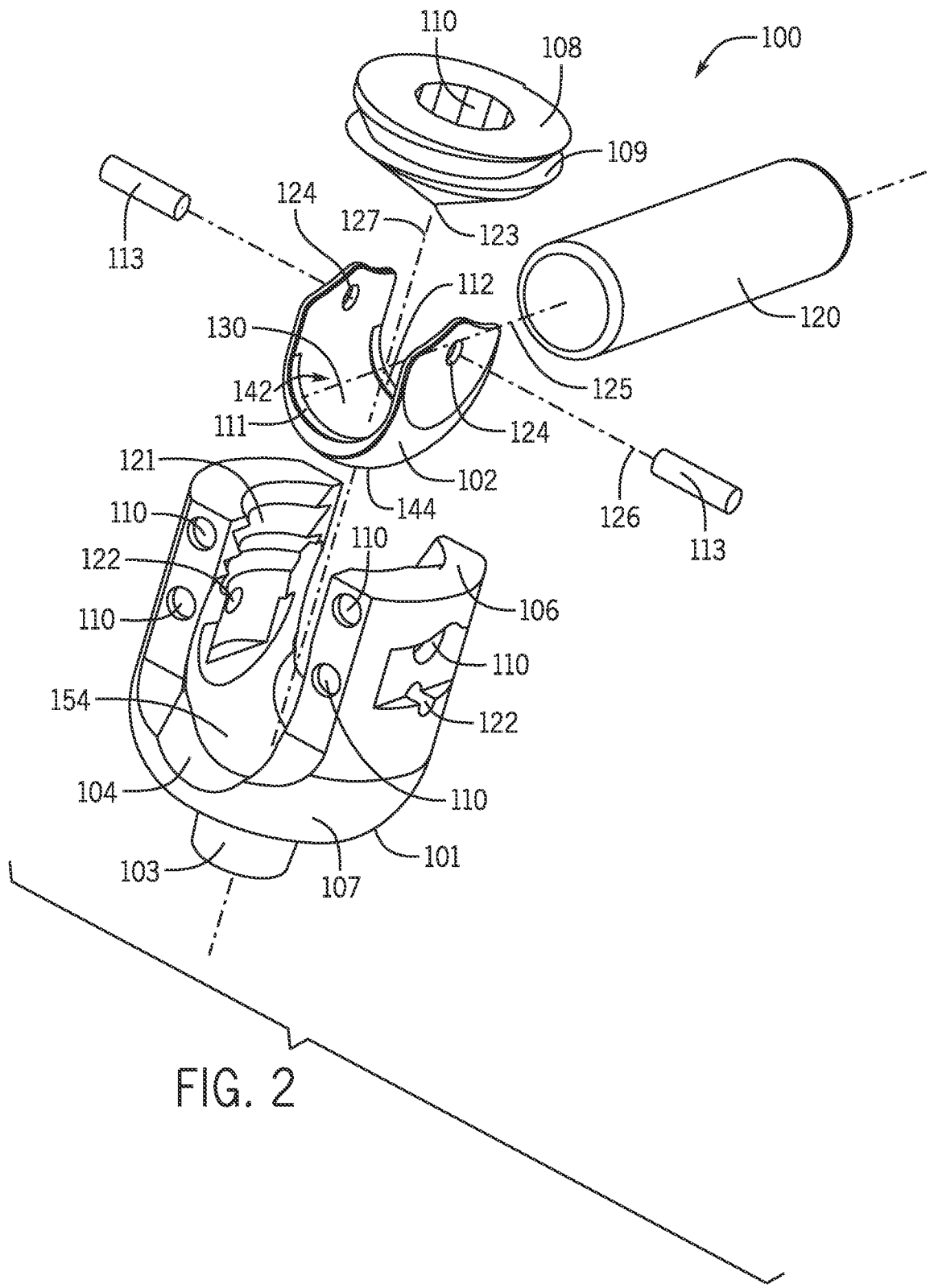
FIG. 2 is an exploded, perspective view of the bone attachment assembly of FIG. 1B.

The crown or top region 106 of the attachment head 101 may provide an opening into the top of the channel 104 for a set screw 108 to be inserted into, as described further herein. Accordingly, as shown in FIGS. 1C and 2, the sidewalls 105 may include internal threads 121 along or within the channel 104 configured to receive and engage with a threaded portion 109 of the set screw 108. The top region 106 and the base region 107 may be on opposite ends of the attachment head 101.

Figure 11:
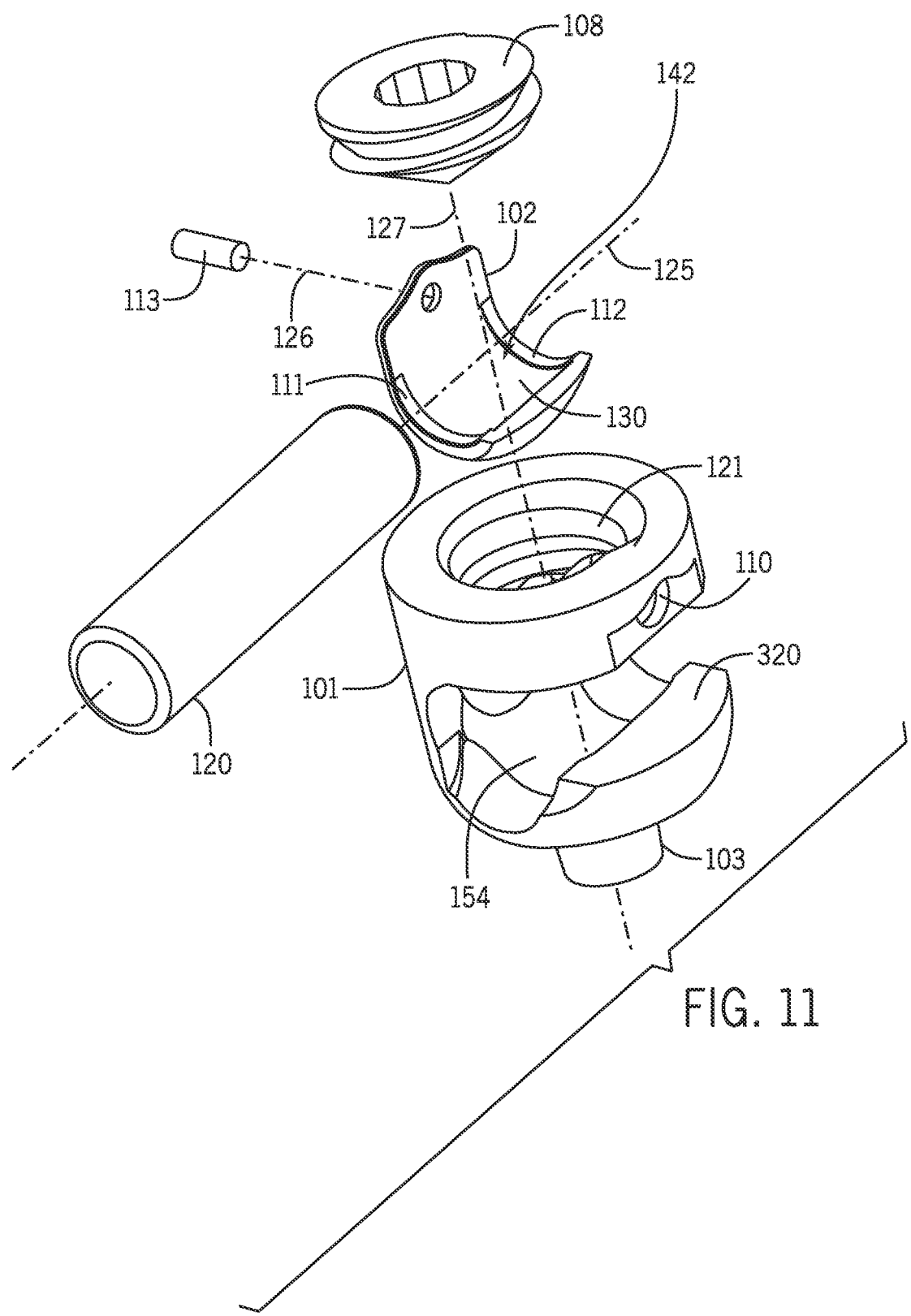
FIG. 11 is an exploded view of a bone attachment assembly according to another embodiment.

As shown in FIG. 1A, the attachment head 101 may be a top-loading attachment head, where the rod 120 is inserted through an opening in the top region 106 of the attachment head 101. Alternatively, as shown in FIG. 11, the attachment head 101 may be a side-loading attachment head, where the rod 120 is inserted through an opening 320 in the side of the attachment head 101. The rod carrier 120 may also be side-loading and accordingly may only have one sidewall.

The base region 107 of the attachment head 101 may provide an area for attaching the threaded screw shaft 103, as shown in FIG. 1C. Accordingly, the threaded screw shaft 103 may extend from the base region 107 of the attachment head 101. According to one embodiment, the attachment head 101 and the screw shaft 103 may be manufactured from a single piece of stock or material, such as metal stock. According to another embodiment, the attachment head 101 and the screw shaft 103 may be separate components and thus may be manufactured separately and later assembled or connected together.

According to one embodiment and as shown in FIGS. 1A and 1C, the sidewalls 105 may include a lower section 115A and an upper section 115B. The upper section 115B may be sidewall extensions that extend from the lower section 115A away from the base region 107 and toward the top region 106 of the attachment head 101. The upper section 115B may be configured to break away from the lower section 115A along notched regions 116 such that only the lower section 115A of the sidewalls 105 remains a part of the attachment head 101.

Figure 10A:
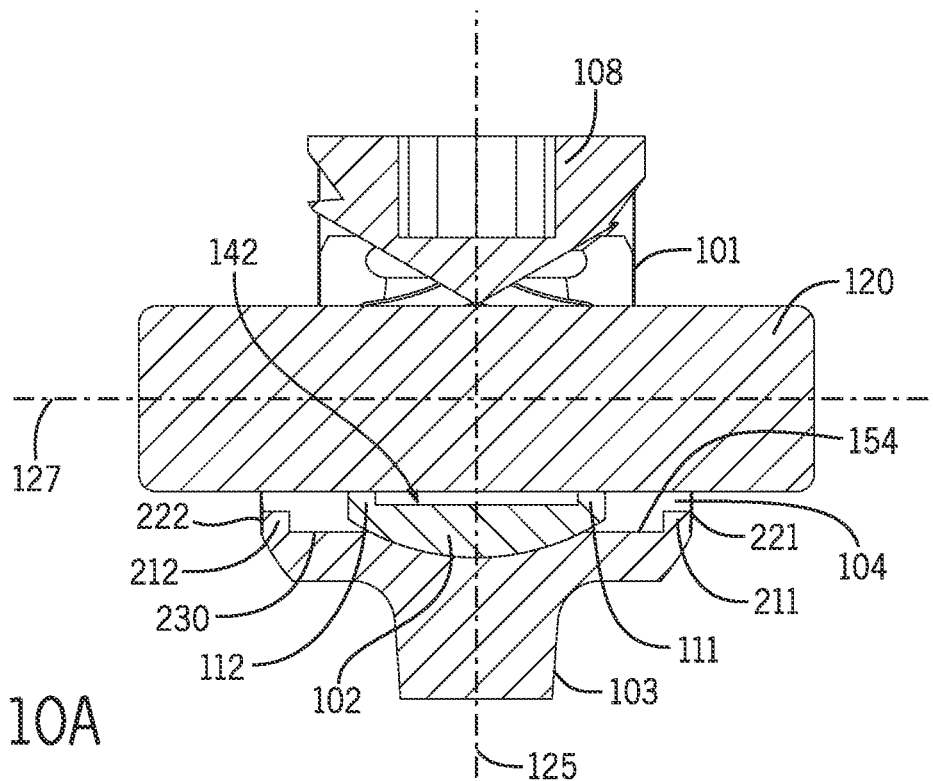
FIG. 10A is a cross-sectional view of a bone attachment assembly according to another embodiment in a first position.
Figure 10B:
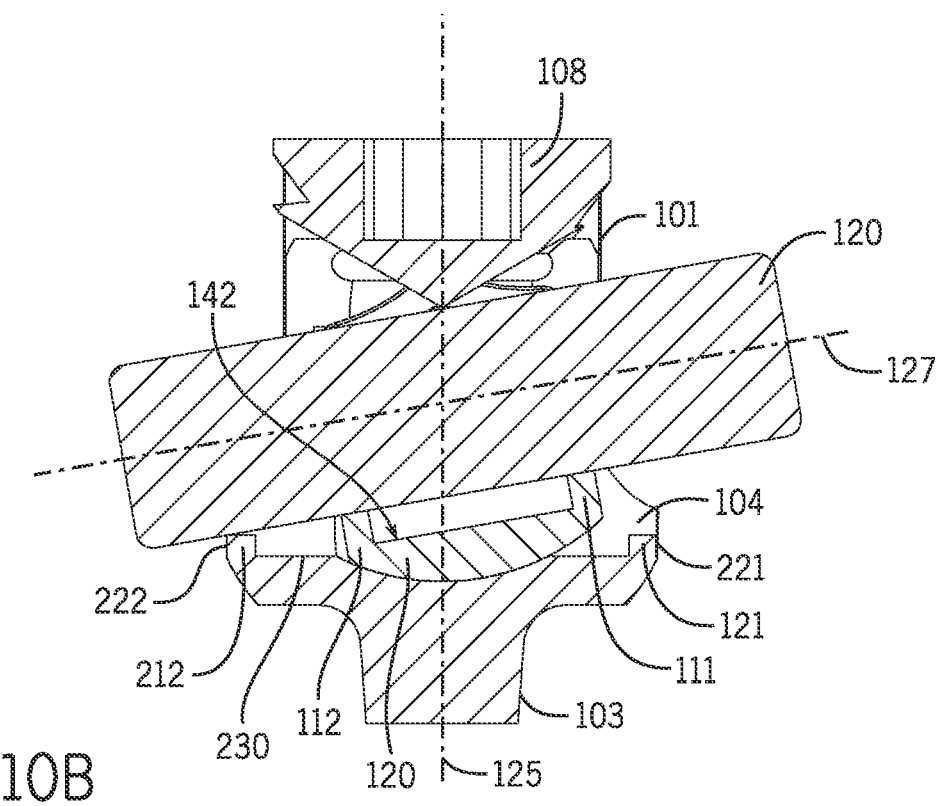
FIG. 10B is a cross-sectional view of the bone attachment assembly of FIG. 10B in a second position.

According to another embodiment as shown in FIGS. 10A-10B, the channel 104 of the attachment head 101 may include a first raised section 211 and a second raised section 212 that defined a lowered section 230 positioned between the first raised section 211 and the second raised section 212. The first raised section 211 may be formed on a first peripheral edge 221 of the inner surface 154 of the channel 104 and the second raised section 212 may be formed on a second peripheral edge 222 of the inner surface 154 of the channel 104. Accordingly, the rod carrier 102 (as described further herein) may be positioned between the first raised section and the second raised section of the channel 104. Therefore, when the rod 120 and the rod carrier 102 have been moved in one direction to their fullest extent as shown in FIG. 10B (e.g., the longitudinal rod axis 125 of the rod 120 is not perpendicular to the longitudinal screw axis 127 of the threaded screw shaft 103), the first raised section 211 or the second raised section 212 may directly abut or contact the rod 120, thus creating four points of contact of the rod 120 within the attachment head 101 and increasing the frictional hold of the rod 120 within the attachment head 101.

Set Screw

The bone attachment assembly 100 may further include a rod fastener or set screw 108 that is configured to attach to the attachment head 101. More specifically, the set screw 108 may be positioned or inserted into the opening within the top region 106 of the attachment head 101 and may be advanced within the channel 104 from the top region 106 toward the base region 107 and thus toward a rod 120 which has been positioned within the channel 104 of the attachment head 101. Accordingly, the set screw 108 may be advanced along the longitudinal screw axis 127 toward the base region 107 of the attachment head 101 when the set screw 108 is threadably coupled into internal threads 121 of the attachment head 101.

The set screw 108 may include a fulcrum tip, pointed base, or pointed tip 123 at the base of the set screw 108 that is configured to directly contact and apply a point load to a top portion of the rod 120 when the rod 120 is on the rod surface 142 (and within the rod carrier 102 and/or the attachment head 101). The set screw 108 preferably does not have a flat base. The pointed tip 123 may bias the rod 120 toward and against the rod surface 142 to hold the rod 120 in place within the attachment head 101. Accordingly, as shown in FIGS. 1C and 2, advancing the set screw 108 toward the rod 120 causes the pointed tip 123 of the set screw 108 to engage with the rod 120 seated on the rod surface 142 (and within the rod carrier 102 and/or the attachment head 101).

In order to attach the set screw 108 to the attachment head 101 and position the set screw 108 within the channel 104, the set screw 108 may include an outer threaded portion 109 to engage or threadably couple with the internal threads 121 of the sidewalls 105 of the attachment head 101. Accordingly, the set screw 108 may be screwed along the height of the sidewalls 105 (and thus the channel 104) to move the set screw to the rod 120 and to secure the rod 120 in place (as described further herein).

In order to move the set screw 108, the set screw 108 may include a torque applicator tool recess 110 in the top of the set screw 108. The torque applicator tool recess 110 may be shaped to receive at least a portion of a torque applicator tool, such as a screw driver, clamp, or wrench, in order to move the set screw 108 along the height of the sidewalls 105. Alternatively or additionally, the bone attachment assembly 100 may include torque applicator tool recesses 110 in other areas, such as along the outer surfaces of the sidewalls 105, as shown in FIG. 2.

According to another embodiment as shown in FIGS. 6A-6D, the bone attachment assembly 700 may include a threaded screw shaft 703, an attachment head 701, and a set screw 708 that is received or engaged within a set screw receiver 709. The set screw 703 can have external threads that mate with internal threads on the set screw receiver 709. The set screw receiver 709 is configured to be coupled with and rotationally locked to the top region 706 of the sidewalls 705 of the attachment head 701 by conventional structures. The set screw receiver 709 can be configured so as to prevent the sidewalls 705 from splaying. The sidewalls 705 form the channel 704 that is configured to receive and house the rod carrier 702 and a rod. The set screw 708 can be inserted through the set screw receiver 709 to retain the rod 120 in position.

Rod Carrier

In order to retain the rod 120 and allow the position of the rod 120 to be adjusted within the attachment head 101, the bone attachment assembly 100 may optionally include a rod carriage or a rod carrier 102 positioned within the channel 104 of the attachment head 101. The rod carrier 102 may be configured to receive and hold the rod 120 within the attachment head 101 such that the rod 120 is retained between the rod carrier 102 and the set screw 108 within the attachment head 101.

In an unloaded state, the rod carrier 102, with the rod 120, may be freely movable and adjustable within the attachment head 101. The unloaded state may refer to when the set screw 108 is not firmly pressed against or tightened or on the rod 120. Accordingly, in the unloaded state, the rod 120 is movably (e.g., pivotally or slidably) retained by the rod carrier 102 within the channel 104 when the rod 120 is positioned between the rod carrier 102 and the set screw 108 and before the set screw 108 is firmly pressed against the rod 120.

In a loaded state, the rod carrier 102, and thus the rod 120, may be fixed in position within the attachment head 101. The loaded state may refer to when the rod 120 is positioned within the attachment head 101 and the set screw 108 is firmly pressed against or tightened on the rod 120 in order to secure the rod 120 into position within the attachment head 101. Accordingly, in the loaded state, the rod 120 and the rod carrier 102 are fixed and not movable within the channel 104 when the set screw 108 is tightened on the rod 120.

Figure 4B:
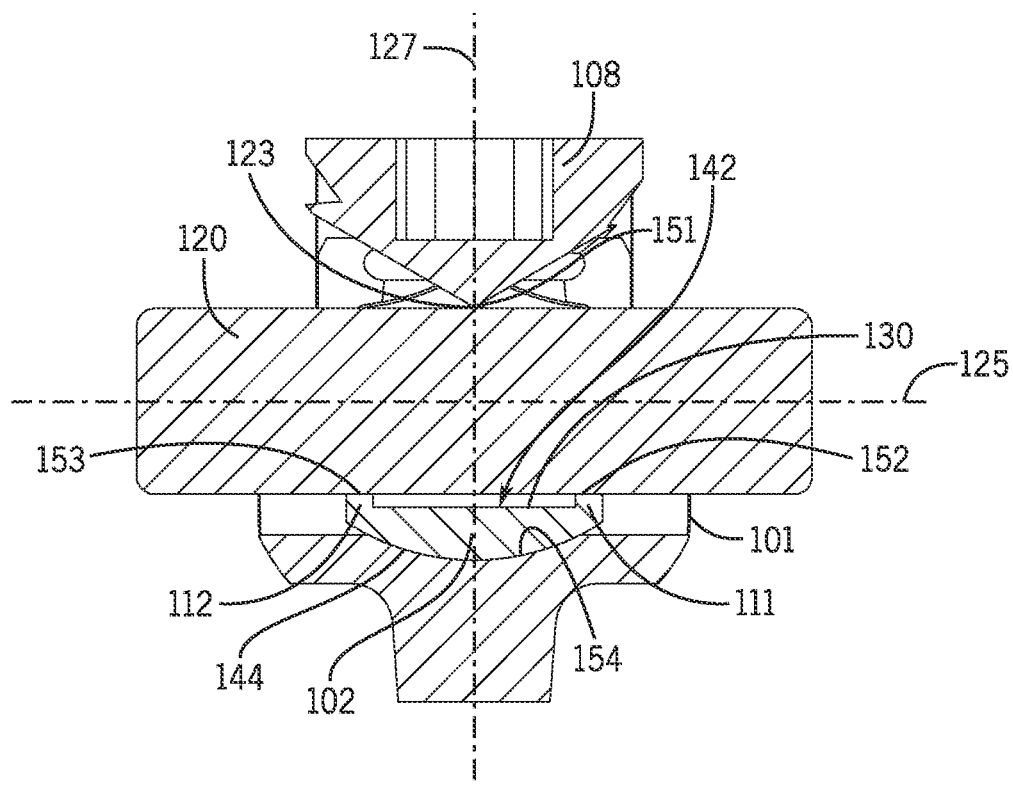
FIG. 4B is a cross-sectional view of the bone attachment assembly of FIG. 4A.
Figure 5B:
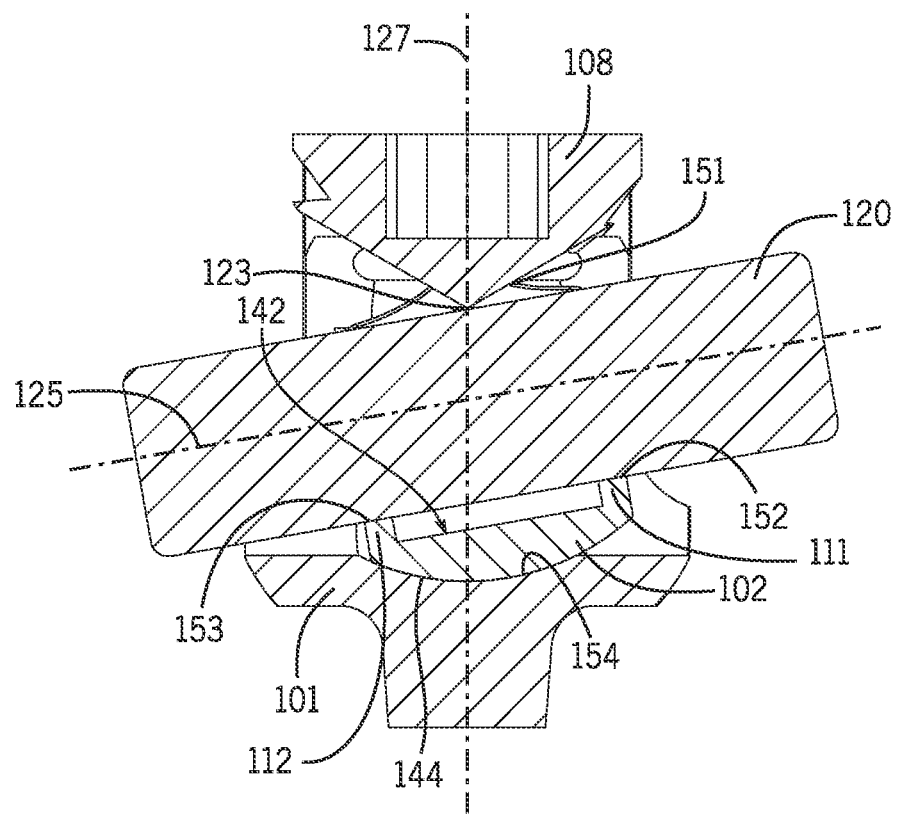
FIG. 5B is a cross-sectional view of the bone attachment assembly of FIG. 5A.

More specifically and as shown in FIGS. 2, 4B, and 5B, due to the set screw 108 tightening against the rod 120 and thus pressing the rod 120 and the rod carrier 102 toward the base region 107 of the attachment head 101, a lower convex surface 144 of the rod carrier 102 may abut and further press against an inner concave surface 154 within the channel 104 of the attachment head 101. Accordingly, friction between the lower convex surface 144 of the rod carrier 102 and the inner concave surface of the attachment head 101 may prevent or prohibit movement between the rod carrier 102 and the attachment head 101.

According to one embodiment, the rod carrier 102 may be positioned within the channel 104 of the attachment head 101 that is formed by the sidewalls 105 of the attachment head 101. Accordingly, the rod carrier 102 may be movably coupled to a portion of the attachment head 101, such as to the sidewalls 105 of the channel 104. Depending on the configuration of the rod carrier 102, the rod carrier 102 may be pivotally or slidably coupled to the attachment head 101.

For example, when the rod 120 is positioned within the channel 104 of the attachment head 101, the rod carrier 102 may be positioned such that the longitudinal rod axis 125 of the rod 120 is substantially perpendicular to the longitudinal screw axis 127 in a "neutral position," as shown in FIGS. 4A-4B. However, the rod carrier 102 may be moved (e.g., pivoted, rotated, or slide), such that the longitudinal rod axis 125 of the rod 120 is not substantially perpendicular to the longitudinal screw axis 127. For example, as shown in FIGS. 5A-5B, the rod 120 and the rod carrier 102 have been rotated by approximately 10 degrees in one direction to their full extent by pivoting the rod carrier 102 via the pins 113 about the lateral axis 126.

According to one embodiment, the rod carrier 102 may pivotally coupled to the attachment head 101. Accordingly, as shown in FIGS. 3A-3C, the rod carrier 102 may be configured as a "swing" within the attachment head 101 and may be substantially u-shaped such that the rod carrier 102 is configured to surround a lower portion and two sides of the rod 120. As shown in FIG. 1C, the rod carrier 102 may be configured to rotate or pivot about a lateral axis 126 of the bone attachment assembly 100 that extends through the pins 113. The lateral axis 126 may be substantially perpendicular to the longitudinal screw axis 127 and may be a transverse axis relative to spine.

The rod carrier 102 may be pivotally coupled to the attachment head 101 via pins 113 extending into the sidewalls 105 of the attachment head 101, as shown in FIGS. 1C and 2. Accordingly, the sidewalls 105 of the attachment head 101 may include pin recesses, slots, or apertures 122, each configured to receive and retain a first end of the pin 113 in the sidewalls 105 of the attachment head 101. The apertures 122 may be substantially opposite each other and positioned at substantially the same height. Similarly, the rod carrier 102 may also include pin recesses, slots, or apertures 124, each configured to receive and retain a second end of the pin 113 in a portion of the rod carrier 102. The apertures 124 may be substantially opposite each other and positioned at substantially the same height. As shown in FIG. 3A, the apertures 124 may be at a top portion of the rod carrier 102. However, it is anticipated that the apertures 124 may be at a middle or lower portion of the rod carrier 102.

According to one embodiment, the pins 113 may be fixed to the rod carrier 102 and rotate within the apertures 122 of the attachment head 101. Alternatively, the pins 113 may be fixed to the attachment head 101 and rotate within the apertures 124 of the rod carrier 102. According to one embodiment, the apertures 122 and 124 may be oversized relative to the pins 113 such that the rod carrier 102 may slightly translate in addition to rotate.

Figure 6A:
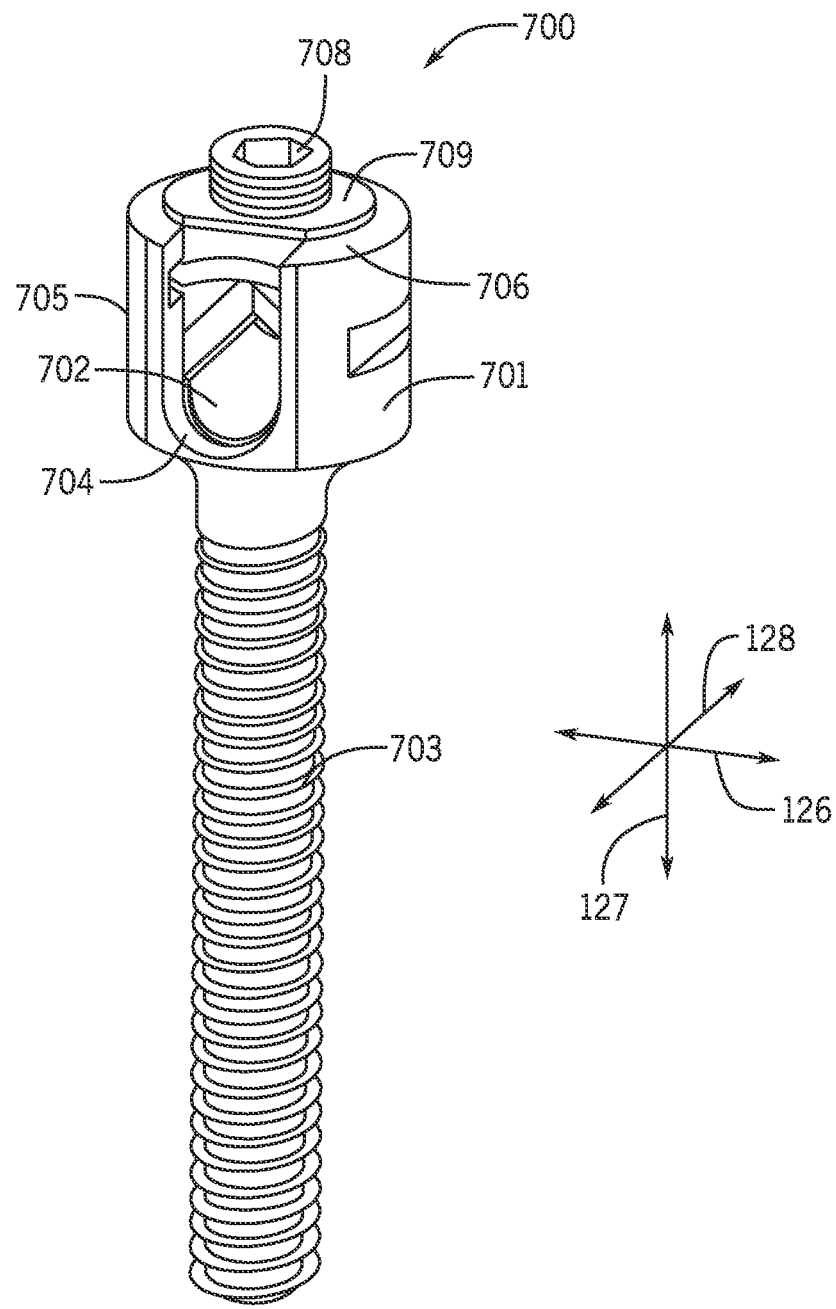
FIG. 6A is a perspective view of a bone attachment assembly according to another embodiment.
Figure 6B:
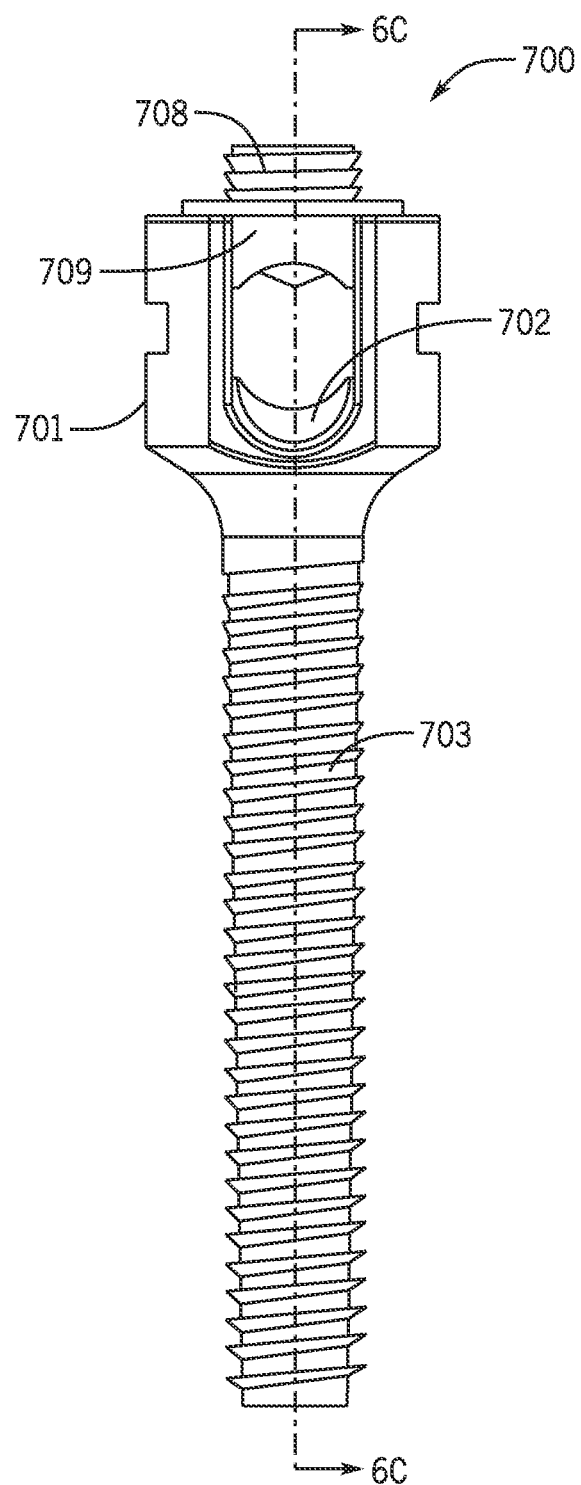
FIG. 6B is an end view of the bone attachment assembly of FIG. 6A.
Figure 6C:
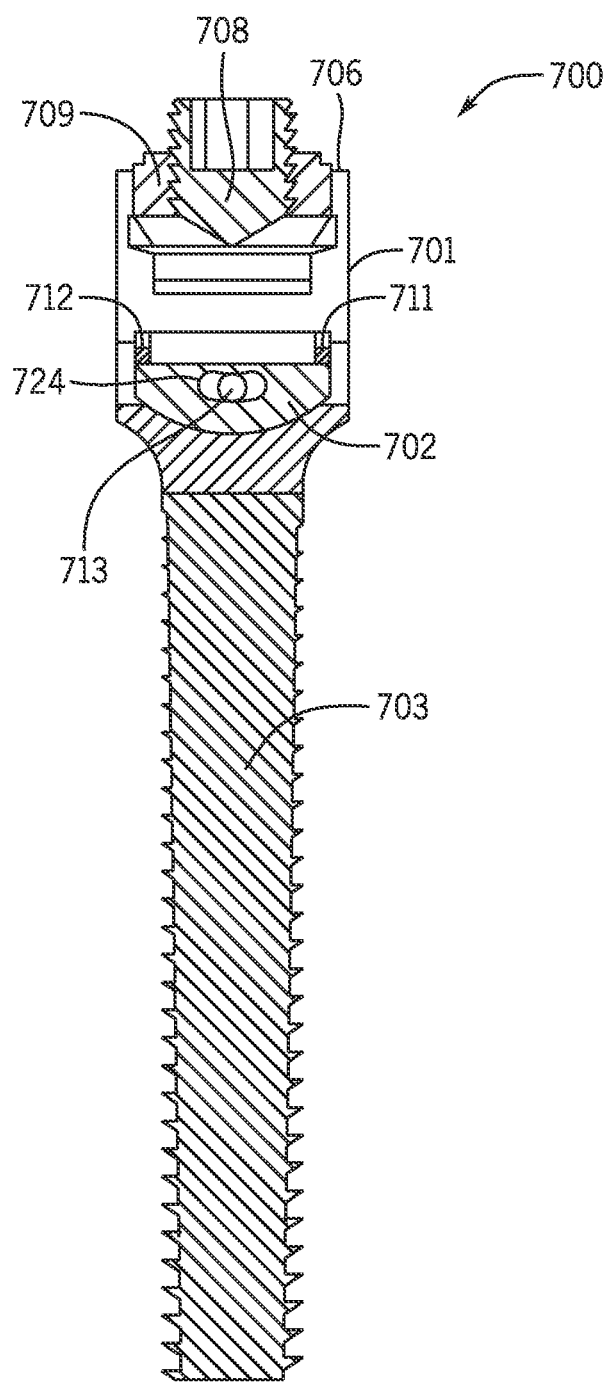
FIG. 6C is a cross-sectional, side view of FIG. 6B along line 6C-6C.
Figure 6D:
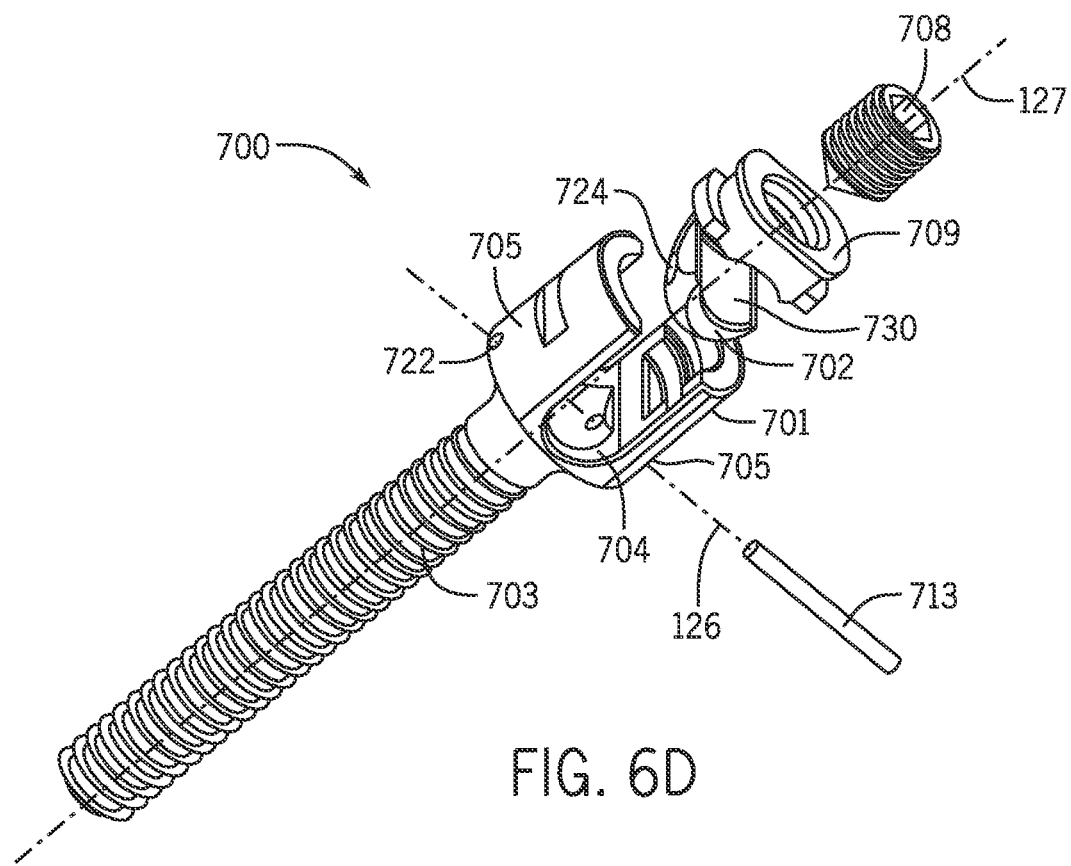
FIG. 6D is an exploded, perspective view of the bone attachment assembly of FIG. 6A.

According to another embodiment as shown in FIGS. 6A-6D, the rod carrier 702 may be slidably coupled to the attachment head 701. As shown in FIG. 6A, the rod carrier 702 may be configured to slide within the attachment head 701 along an axis 128 that is substantially perpendicular to the lateral axis 126 and the longitudinal screw axis 127. As shown in FIGS. 6C-6D, the rod carrier 702 may include a pin recess, aperture, or slot 724 that is configured to receive a connecting pin 713. As shown, the slot 724 may be curved to match the shape of the lower convex surface 144 of the rod carrier 102. The attachment head 701 may also include pin recesses, slots, or apertures 722 for receiving the pin 713. The pin 713 may optionally extend through the channel 704 of the attachment head 701.

Accordingly, the rod carrier 702 may be configured to slide on the pin 713 such that the pin 713 moves within the slot 724 in order to adjust the position of the rod carrier 702 and thus the rod.

According to one embodiment, the rod surface may be a part of the rod carrier 702. Accordingly, a first raised portion 711 and a second raised portion 712 of the rod surface may be on the rod carrier 702 and may define a lowered portion 730 on the rod carrier 702 between the first raised portion 711 and the second raised portion 712. As used herein, the raised portions 711, 712 are raised in the sense that they are positioned relative to the lowered portion 730 such that the raised portions 711, 712 will contact the rod 120 while the lowered portion 730 will remain spaced from the rod 120. As described further herein, the set screw 708, the first raised portion 711, the second raised portion 712 (with the lowered portion 730) facilitate a three-point fixation of the rod 120.

According to one embodiment as shown in FIG. 1B, the rod carrier 102 may include a cannula aperture 117 in order to provide access to the cannula conduit 114 in the screw shaft 103. The cannula aperture 117 may optionally extend through the lowered portion 130. Accordingly, the cannula conduit 114 and the cannula aperture 117 may accommodate insertion of a device, such as a guide-wire or other equipment components, or substances.

However, it is understood that the bone attachment assembly may not include a rod carrier 102, as shown in FIG. 12. Instead, the rod 120 may be positioned directly within the attachment head 101.

The Rod Surface

The bone attachment assembly 100 may include a rod surface 142 that is configured to directly hold the rod 120 within the attachment head 101. According to one embodiment as shown in FIGS. 3A-5B, the rod surface 142 may be a part of the rod carrier 102. Accordingly, the rod surface 142 and the lower convex surface 144 of the rod carrier 102 may be opposite each other through a wall of the rod carrier 102 such that the rod surface 142 faces the rod 120 and the lower convex surface 144 faces the attachment head 101. According to another embodiment as shown in FIG. 12, the bone attachment assembly 100 may not include a rod carrier 102 and the rod surface 142 may be a part of the attachment head 101.

The rod surface 142 may be shaped to correspond to the shape of the rod 120 in order to support and receive the rod 120. According to one embodiment, the rod surface 142 may be curved or substantially concave to match the curvature or round perimeter of the rod 120, as shown in FIGS. 1C and 3B. According to another embodiment, the rod surface 142 may include a rectangular or square profile (e.g., box shaped) in order to receive a rod 120 that is rectangular, square, or I-beam shaped.

As shown in FIG. 4B, the rod surface 142 may include a first raised portion 111 and a second raised portion 112 that are configured to directly abut or contact the rod 120 and to further retain the rod 120 within the attachment head 101. The rod 120 may be seated along both the first raised portion 111 and the second raised portion 112. According to one embodiment, the first raised portion 111 may be formed along a first peripheral edge of the rod carrier 102 or the attachment head 101 and the second raised portion 112 may be formed along a second peripheral edge of the rod carrier 102 or the attachment head 101. Accordingly, as shown in FIGS. 3A and 3C, the first peripheral edge and the second peripheral edge may be substantially opposite each other with the lowered portion 130 therebetween.

Figure 7:
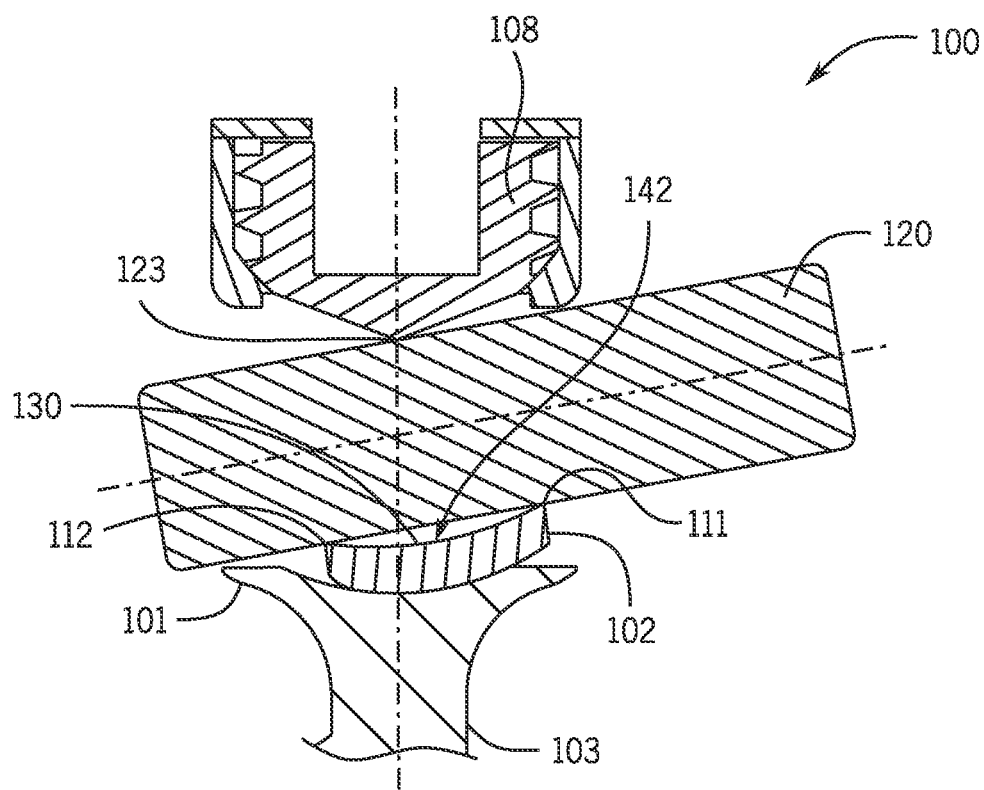
FIG. 7 is a cross-sectional view of a bone attachment assembly according to another embodiment.

According to various embodiments, the first and second raised portions 111 and 112 may be slightly rounded or filleted. According to one embodiment as shown in FIG. 3C, the first raised portion 111 and the second raised portion 112 may be ridges that extend along a width of the rod surface 142. Accordingly, the first and second raised portions 111 and 112 may extend in stepwise fashion above the lowered portion 130 (as described further herein). According to another embodiment as shown in FIG. 7, the rod surface 142 (and optionally the rod carrier 102) may have a "scalloped design." Accordingly, the rod surface 142 may be curved or beveled such that the lowered portion 130 slopes from or is gradually ramped from each of the first and second raised portions 111 and 112. This embodiment may decrease the applied stress to the rod 120 and may reduce the corrosion (particularly with stainless steel implants). Furthermore, the "scalloped design" may reduce the amount of notching or deforming to the rod 120.

According to one embodiment as shown in FIG. 3C, the width W of the first raised portion 111 and the second raised portion 112 may be between approximately 0.60 millimeters and 1.00 millimeter. According to another embodiment, the width W of the first raised portion 111 and the second raised portion 112 may be approximately 0.81 millimeters.

As shown in FIG. 3C, the first raised portion 111 and the second raised portion 112 define a recess or lowered portion 130 positioned between the first raised portion 111 and a second raised portion 112. When the rod 120 is placed on a portion of the rod surface 142 (and optionally within the rod carrier 102 and/or the attachment head 101 such that the rod carrier 102 or the attachment head 101 receives the rod 120), the rod 120 is positioned directly on the first raised portion 111 and the second raised portion 112 and may extend or reside over the lowered portion 130. Accordingly, when the set screw 108 is tightened against the rod 120, the rod 120 may flex or bend into the lowered portion 130.

According to one embodiment as shown in FIG. 3C, the depth D of the lowered portion 130 (e.g., the distance between the lowered portion 130 and the first and second raised portions 111 and 112) may be between approximately 0.20 millimeters and 0.60 millimeters. According to another embodiment, the depth D of the lowered portion 130 may be approximately 0.40 millimeters. According to a further embodiment, the depth D of the lowered portion 130 may be between approximately 0.05 millimeters and 0.20 millimeters. According to yet another embodiment, the depth D of the lowered portion 130 may be approximately 0.10 millimeters.

The rod carrier 102 may be composed of various materials including, but not limited to, stainless steel, titanium, and cobalt-chrome. The rod carrier 102 may be composed of the same material as the attachment head 101 or may be composed of a material distinct from the material of the attachment head 101. Similarly, the first raised portion 111 and the second raised portion 112 of the rod surface 142 may be composed of a material distinct from the rod carrier 102 and the attachment head 101. For example, the first raised portion 111 and the second raised portion 112 may be composed of a material having a greater hardness than the rod carrier 102 in order increase the structural integrity of the first raised portion 111 and the second raised portion 112. As a further alternative, the raised portions 111, 112 may be treated in such a manner as to selectively increase their hardness relative to the rod carrier 102. Accordingly, the first raised portion 111 and the second raised portion 112 may be able to handle more load from the rod 120.

Three-Point Fixation

The rod 120 may be seated within the attachment head 101 between the set screw 108 and the rod surface 142. As shown in FIGS. 4B and 5B, the rod 120 may be specifically positioned between the set screw 108 and the rod surface 142 on the rod carrier 102. As shown in FIG. 12, the rod 120 may be specifically positioned between the set screw 108 and the rod surface 142 on the attachment head 101. Accordingly, the first raised portion 111, the second raised portion 112, and the set screw 108 directly contact the rod 120 in order to retain the rod within the attachment head 101 and the rod 120 may be held in three-point fixation between the pointed tip 123 of the set screw 108, the first raised portion 111 of the rod surface 142, and the second raised portion 112 of the rod surface 142. As shown in FIGS. 4B and 5B, the three-point fixation may be maintained as the position of the rod 120 and the rod carrier 102 is adjusted. For example, as the rod 120 is rotated or pivoted with the rod carrier 102 such that the longitudinal rod axis 125 is not substantially perpendicular to the longitudinal screw axis 127 (as shown in FIG. 5B), the rod 120 remains in the three-point fixation at contact points 151, 152, and 153 within the attachment head 101.

When the rod 120 is positioned on the rod surface 142 (and optionally within the rod carrier 102), the three points of contact of the rod 120 within the attachment head 101 are defined by the pointed tip 123, the first raised portion 111, and the second raised portion 112. The interface between the pointed tip 123 and the rod 120 defines an intermediate contact point 151, the interface between the first raised portion 111 and the rod 120 defines a first lateral contact point 152, and the interface between the second raised portion 112 and the rod 120 defines a second lateral contact point 153.

When the longitudinal rod axis 125 of the rod 120 is substantially perpendicular to the longitudinal screw axis 127 of the threaded screw shaft 103 and as the rod 120 and the rod carrier 102 are being adjusted, the rod 120 may be secured or held within the attachment head 101 by only the three points of contact. Optionally, when the rod 120 and the rod carrier 102 are moved to the full extent in one direction (as shown in FIG. 5B), the attachment head 101 may be configured to provide a fourth contact point to the rod 120. Alternatively, it is also anticipated that the attachment head 101 may be configured such that the rod 120 does not directly contact the attachment head 101 when the rod 120 and the rod carrier are moved to the full extend in one direction.

The three-point fixation may allow higher contact forces to be applied at the first lateral contact point 152 and the second lateral contact point 153 than if the rod 120 were supported along its entire length on a rod surface within the rod carrier 102 or the attachment head 101. Furthermore, the three-point fixation may allow the rod 120 to flex or bend into the lowered portion 130 under high stresses, thus achieving a three-point bending of the rod 120. Even further, the three-point fixation increases the slide resistance of the rod 120 (thus preventing the rod 120 from inadvertently sliding, moving, or being adjusted) while still allowing the rod 120 to be moved or adjusted within the attachment head 101 before securing the rod 120 in place.

Method of Assembling a Bone Attachment Assembly

Figure 8:
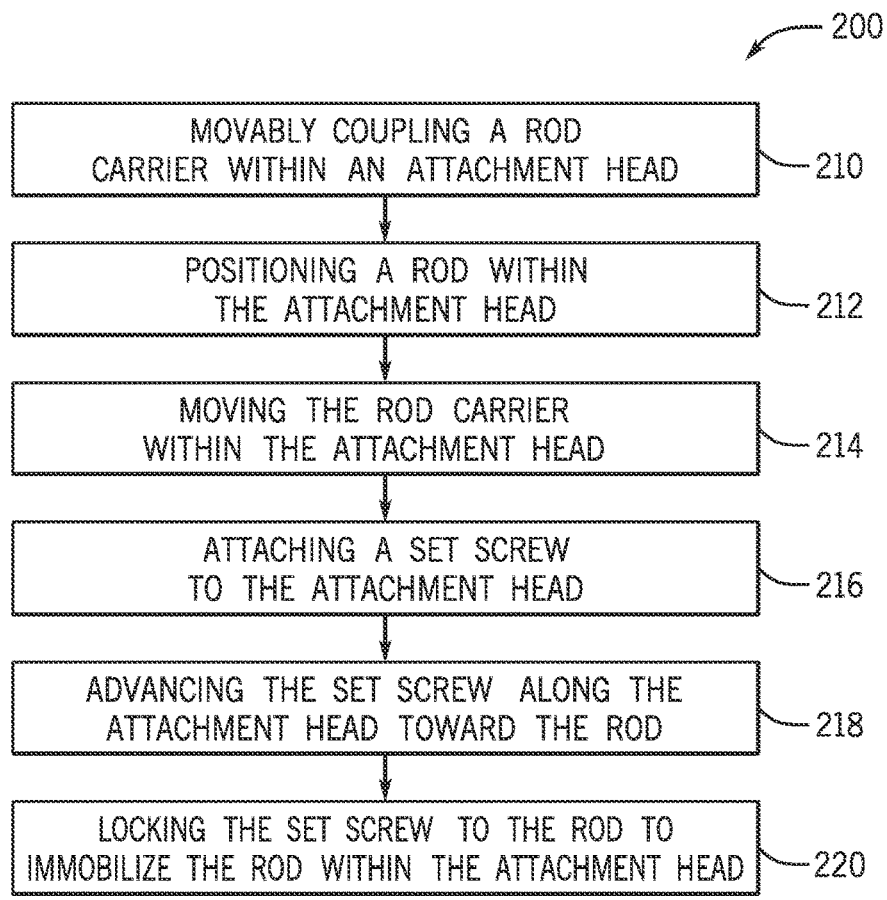
FIG. 8 is a schematic representation of a method of assembling a bone attachment assembly according to one embodiment.

As shown in FIG. 8, a method 200 of assembly a bone attachment assembly 100 may optionally include a step (210) of movably coupling the rod carrier 102 within the attachment head 101 and may include a step (212) of positioning the rod 120 within the attachment head 101 such that the rod 120 directly contacts the first raised portion 111 and the second raised portion 112 of the rod surface 142. The method 200 may further include a step (214) of moving the rod carrier 102 within the attachment head 101 such that the angle of the longitudinal rod axis 125 of the rod 120 is adjusted relative to the longitudinal screw axis 127 of the threaded screw shaft 103. The method 200 may also include a step (216) of attaching the set screw 108 to the attachment head 101 and a step (218) of advancing the set screw 108 along the attachment head 101 toward the rod 120 such that the attachment head 101 (such as the pointed tip 123 of the attachment head 101 directly contacts and applies a point load to the rod 120. Accordingly, the first raised portion 111, the second raised portion 112, and the set screw 108 may retain the rod 120 within the attachment head 101. As the rod carrier 102 and the rod 120 are moved within the attachment head 101, the three points of contact (of the rod 120 with the first raised portion 111, the second raised portion 112, and the set screw 108) are maintained. The method 200 may also include a step (220) of tightening and locking the set screw 108 to the rod 120 to immobilize the rod 120 (and the rod carrier 102) within the attachment head 101 such that the rod 120 is fixed in place with three points of contact. Accordingly, the three points of contact are further configured to cause a three-point bending of the rod 120 as the set screw 108 is advanced along the attachment head 101 and compresses the rod 120 toward the first raised portion 111 and the second raised portion 112.

As utilized herein, the terms "approximately," "about," "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

The embodiments disclosed herein provide a bone attachment assembly with a three-point attachment to a connecting rod. Besides those embodiments depicted in the figures and described in the above description, other embodiments of the present invention are also contemplated. For example, any single feature of one embodiment of the present invention may be used in any other embodiment of the present invention.

Given the disclosure of the present invention, one versed in the art would appreciate that there may be other embodiments and modifications within the scope and spirit of the invention. Accordingly, all modifications attainable by one versed in the art from the present invention within the scope and spirit of the present invention are to be included as further embodiments of the present invention.

What is claimed is:

1. A bone attachment assembly comprising: an attachment head;
a set screw configured to attach to the attachment head; and
a rod carrier pivotably coupled to the attachment head and having a rod surface with a first raised portion and a second raised portion that define a lowered portion positioned between the first raised portion and the second raised portion, wherein the rod carrier is pivotable about a lateral axis perpendicular to an axis of the attachment head,
wherein the first raised portion, the second raised portion, and the set screw are configured to directly contact a rod in order to retain the rod within the attachment head,
wherein a threaded screw shaft is attached to a base region of the attachment head, wherein, when the rod is positioned on a portion of the rod surface and the longitudinal axis of the rod is substantially perpendicular to the longitudinal axis of the threaded screw shaft, the first raised portion, the second raised portion, and a pointed tip of the set screw define three points of contact of the rod within the attachment head, wherein the rod is held within the attachment head by only the three points of contact.

2. The bone attachment assembly of claim 1, wherein the rod surface is configured to receive the rod such that the rod is positioned on the first raised portion and the second raised portion and extends over the lowered portion.

3. The bone attachment assembly of claim 1, wherein the rod carrier is movable within the attachment head in an unloaded state.

4. The bone attachment assembly of claim 3, wherein the attachment head is configured such that the rod carrier is freely movable with the rod within the attachment head when the set screw is not tightened on the rod in the unloaded state, and the rod carrier and the rod are not movable within the attachment head when the set screw is tightened on the rod in the loaded state.

5. The bone attachment assembly of claim 4, wherein the attachment head is configured such that a convex surface of the rod carrier abuts an inner surface of the attachment head such that friction prevents movement between the rod carrier and the attachment head when the set screw is tightened on the rod in the loaded state, wherein the convex surface and the rod surface are opposite each other through a wall of the rod carrier.

6. The bone attachment assembly of claim 3, further comprising a threaded screw shaft attached to a base region of the attachment head, wherein a channel of the attachment head includes a first raised section and a second raised section that define a lowered section positioned between the first raised section and the second raised section, wherein the rod carrier is configured to be positioned between the first raised section and the second raised section, wherein one of the first raised section or the second raised section can abut the rod when the longitudinal axis of the rod is not perpendicular to the longitudinal axis of the threaded screw shaft.

7. The bone attachment assembly of claim 1, wherein the rod surface is a part of the attachment head.

8. The bone attachment assembly of claim 1, wherein the first raised portion and the second raised portion are ridges extending along a width of the rod surface and extending stepwise above the lowered portion.

9. The bone attachment assembly of claim 1, wherein the rod surface is curved such that the lowered portion slopes from each of the first raised portion and the second raised portion.

10. The bone attachment assembly of claim 1, wherein the set screw includes a pointed tip that is configured to directly contact and apply a point load to the rod.

11. The bone attachment assembly of claim 1, further comprising at least one torque applicator recess in at least one of the attachment head and/or the set screw, wherein the at least one torque applicator recess is configured to receive at least a portion of a torque applicator tool.

12. The bone attachment assembly of claim 1, further comprising a connecting rod configured to extend through and be secured within the attachment head such that the connecting rod directly contacts the first raised portion, the second raised portion, and the set screw, wherein the connecting rod is configured to also extend through and be secured within at least one other attachment head of at least one other bone attachment assembly.

13. A method of assembling a bone attachment assembly comprising: pivotably coupling a rod carrier to an attachment head, wherein the rod carrier includes a
rod surface having a first raised portion, a second raised portion, and a lowered portion between the first and second raised portions, wherein the rod carrier is pivotable about a lateral axis perpendicular to an axis of the attachment head;
positioning a rod within the attachment head such that the rod directly contacts the first raised portion and the second raised portion of the rod surface;
attaching a set screw to the attachment head;
advancing the set screw along the attachment head toward the rod such that the set screw directly contacts and applies a point load to the rod, wherein the first raised portion, the second raised portion, and the set screw retain the rod within the attachment head,
moving the rod carrier within the attachment head such that the angle of the longitudinal axis of the rod is adjusted relative to the longitudinal axis of a threaded screw shaft that is attached to a base region of the attachment head, wherein the rod surface is a part of the rod carrier, wherein the first raised portion, the second raised portion, and the set screw define three points of contact of the rod within the attachment head, wherein the three points of contact are maintained as the rod carrier is moved, wherein the three points of contact are configured to cause a three-point bending of the rod as the set screw is advanced along the attachment head.

14. A bone attachment assembly comprising: an attachment head;
a set screw configured to attach to the attachment head; and
a rod carrier pivotably coupled to the attachment head and having a rod surface with a first raised portion and a second raised portion that define a lowered portion positioned between the first raised portion and the second raised portion, wherein the rod carrier is pivotable about a lateral axis perpendicular to an axis of the attachment head,
wherein the first raised portion, the second raised portion, and the set screw are configured to directly contact a rod in order to retain the rod within the attachment head,
wherein the first raised portion and the second raised portion are ridges extending along a width of the rod surface and extending stepwise above the lowered portion.

* * * * *